United States Patent
Kohara et al.

(10) Patent No.: US 9,814,792 B2
(45) Date of Patent: Nov. 14, 2017

(54) METHOD FOR PRODUCING STERILIZED MEDICAL FORMED ARTICLE

(71) Applicant: ZEON CORPORATION, Tokyo (JP)

(72) Inventors: Teiji Kohara, Tokyo (JP); Atsushi Ishiguro, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 14/914,363

(22) PCT Filed: Aug. 29, 2014

(86) PCT No.: PCT/JP2014/072809
§ 371 (c)(1),
(2) Date: Feb. 25, 2016

(87) PCT Pub. No.: WO2015/033876
PCT Pub. Date: Mar. 12, 2015

(65) Prior Publication Data
US 2016/0213796 A1    Jul. 28, 2016

(30) Foreign Application Priority Data

Sep. 6, 2013 (JP) ................. 2013-185292

(51) Int. Cl.
*A61L 2/08* (2006.01)
*C08L 53/02* (2006.01)
*C08K 5/13* (2006.01)

(52) U.S. Cl.
CPC ............. *A61L 2/087* (2013.01); *A61L 2/081* (2013.01); *C08K 5/13* (2013.01); *C08L 53/025* (2013.01)

(58) Field of Classification Search
CPC ...................................... A61L 2/182
USPC ........................................ 422/23
See application file for complete search history.

(56) References Cited

U.S. PATENT DOCUMENTS

| | | | |
|---|---|---|---|
| 2003/0232212 A1* | 12/2003 | Chundury | B32B 27/08 428/515 |
| 2010/0193387 A1* | 8/2010 | Sato | A61L 2/087 206/438 |
| 2013/0008506 A1 | 1/2013 | Tanahashi et al. | |
| 2013/0244367 A1 | 9/2013 | Kohara et al. | |

FOREIGN PATENT DOCUMENTS

| | | |
|---|---|---|
| JP | 2002-121244 A | 4/2002 |
| JP | 2003-082113 A | 3/2003 |
| JP | 2013-048560 A | 3/2013 |
| WO | 00/077094 A1 | 12/2000 |
| WO | 2011/096389 A1 | 8/2011 |
| WO | 2012/043708 A1 | 4/2012 |

OTHER PUBLICATIONS

Nov. 18, 2014 Search Report issued in International Patent Application No. PCT/JP2014/072809.

* cited by examiner

Primary Examiner — Kevin Joyner
Assistant Examiner — Holly Mull
(74) Attorney, Agent, or Firm — Oliff PLC

(57) ABSTRACT

A method is disclosed for producing a sterilized medical formed article that includes applying high-energy rays to a medical formed article at an exposure E. The medical formed article is formed of a resin composition that includes a hydrogenated block copolymer and a phenol-based antioxidant. The hydrogenated block copolymer is obtained by hydrogenating 99% or more of unsaturated bonds of a block copolymer that includes at least two polymer blocks [A] and at least one polymer block [B], the polymer block [A] including a repeating unit derived from an aromatic vinyl compound as a main component, the polymer block [B] including a repeating unit derived from a linear conjugated diene compound as a main component, and a ratio (wA:wB) of a weight fraction wA of the polymer block [A] to a weight fraction wB of the polymer block [B] being 30:70 to 70:30.

3 Claims, No Drawings

METHOD FOR PRODUCING STERILIZED MEDICAL FORMED ARTICLE

TECHNICAL FIELD

The present invention relates to a method for producing a sterilized medical formed article that includes sterilizing a medical formed article by applying high-energy rays, the medical formed article being formed of a resin composition that includes a specific hydrogenated block copolymer and a specific amount of a phenol-based antioxidant.

BACKGROUND ART

A sterilization process that applies high-energy rays has an advantage in that medical formed articles can be sterilized all together in a state in which the medical formed articles are packed in a cardboard box or a plastic case used for transportation, for example. Therefore, such a sterilization process is widely used as a simple and reliable sterilization method.

It is known that a hydrogenated block copolymer that exhibits excellent transparency, heat resistance, flexibility, and the like, and can be sterilized by steam, can suitably be used to produce a medical formed article (e.g., vial, infusion bag, syringe, or culture vessel) (see Patent Literature 1 to 4).

It is known to mix an antioxidant (e.g., phenol-based antioxidant, phosphorus-based antioxidant, or sulfur-based antioxidant) with a hydrogenated block copolymer in order to prevent coloration and a decrease in strength due to oxidative degradation during forming (molding) (see Patent Literature 2 to 4).

Patent Literature 4 discloses that a container produced by forming a hydrogenated block copolymer can be sterilized by applying electron beams or γ-rays.

However, Patent Literature 4 merely discloses that a phosphorus-based antioxidant, a phenol-based antioxidant, a sulfur-based antioxidant, and the like may be used to prevent oxidative degradation that may occur when forming a hydrogenated block copolymer to produce a container, and a phosphorus-based antioxidant is preferable due to a capability to reduce coloration. Patent Literature 4 does not disclose the type and the amount of an antioxidant that is advantageous when sterilizing a container by applying electron beams or γ-rays.

CITATION LIST

Patent Literature

Patent Literature 1: WO00/077094
Patent Literature 2: JP-A-2002-121244
Patent Literature 3: JP-A-2003-82113
Patent Literature 4: JP-A-2013-48560

SUMMARY OF INVENTION

Technical Problem

The inventors of the invention conducted extensive studies regarding the effects of a sterilization process that applies high-energy rays on a medical formed article formed of a hydrogenated block copolymer. As a result, the inventors found that a decrease in pH may occur as a result of the sterilization process when an elution test is performed in accordance with the Japanese Pharmacopoeia 16th Edition (see "Test Methods for Plastic Containers"), and formic acid, acetic acid, and the like may be detected by ion chromatography analysis, for example.

An object of the invention is to provide a method for sterilizing a medical formed article formed of a hydrogenated block copolymer that makes it possible to suppress a situation in which a significant change in pH due to elution in water occurs as a result of a sterilization process that applies high-energy rays.

Solution to Problem

The inventors conducted extensive studies in order to solve the above problems. As a result, the inventors found that it is possible to suppress a situation in which a significant change in pH due to elution in water occurs as a result of a sterilization process when a medical formed article that is formed of a resin composition that includes a specific hydrogenated block copolymer and a specific amount of a phenol-based antioxidant is sterilized by applying high-energy rays. This finding has led to the completion of the invention.

One aspect of the invention provides the following method for producing a sterilized medical formed article (see (1) to (3)).

(1) A method for producing a sterilized medical formed article including applying high-energy rays to a medical formed article at an exposure E, the medical formed article being formed of a resin composition that includes a hydrogenated block copolymer and a phenol-based antioxidant, the hydrogenated block copolymer being obtained by hydrogenating 99% or more of the unsaturated bonds of a block copolymer that includes at least two polymer blocks [A] and at least one polymer block [B], the polymer block [A] including a repeating unit derived from an aromatic vinyl compound as the main component, the polymer block [B] including a repeating unit derived from a linear conjugated diene compound as the main component, and the ratio (wA:wB) of the weight fraction wA of the polymer block [A] in the block copolymer to the weight fraction wB of the polymer block [B] in the block copolymer being 30:70 to 70:30, and the resin composition including the phenol-based antioxidant in a ratio of W to 0.50 parts by weight based on 100 parts by weight of the hydrogenated block copolymer, W being calculated by the following expression (1), $$W = [0.46 \times (100-H) + 0.04] \times (E/25) \quad (1)$$

where, W is the ratio (parts by weight) of the phenol-based antioxidant based on 100 parts by weight of the hydrogenated block copolymer, H is the hydrogenation rate (%) of the hydrogenated block copolymer, H is a numerical value from 99 to 100, and E is the exposure (kGy) of the high-energy rays.

(2) The method for producing a sterilized medical formed article according to (1), wherein the high-energy rays are γ-rays or electron beams.

(3) The method for producing a sterilized medical formed article according to (1), wherein the high-energy rays are applied in a state in which the medical formed article is contained in an airtight container that is formed of a resin film.

Advantageous Effects of Invention

The method for producing a sterilized medical formed article according to one aspect of the invention thus produces a sterilized medical formed article that is formed of a hydrogenated block copolymer while making it possible to suppress a situation in which a significant change in pH due to elution in water occurs as a result of the sterilization process that applies high-energy rays.

DESCRIPTION OF EMBODIMENTS

Exemplary embodiments of the invention are described in detail below.

A method for producing a sterilized medical formed article according to one embodiment of the invention includes sterilizing a medical formed article by applying high-energy rays, the medical formed article being formed of a resin composition that includes a specific hydrogenated block copolymer and a specific amount of a phenol-based antioxidant.

1. Hydrogenated Block Copolymer (1) Block Copolymer (C)

A block copolymer (hereinafter may be referred to as "block copolymer (C)") that is used as a precursor for the hydrogenated block copolymer (hereinafter may be referred to as "hydrogenated block copolymer [1]") used in connection with the embodiments of the invention is a polymer that includes at least two polymer blocks [A] and at least one polymer block [B].

The polymer block [A] includes a structural unit (repeating unit) derived from an aromatic vinyl compound as the main component. The content of the structural unit derived from the aromatic vinyl compound in the polymer block [A] is normally 90 wt % or more, preferably 95 wt % or more, and more preferably 99 wt % or more.

The polymer block [A] may include a component other than the structural unit derived from the aromatic vinyl compound. Examples of the component other than the structural unit derived from the aromatic vinyl compound include a structural unit derived from a linear conjugated diene compound and/or a structural unit derived from an additional vinyl compound. The content of the component other than the structural unit derived from the aromatic vinyl compound in the polymer block [A] is normally 10 wt % or less, preferably 5 wt % or less, and more preferably 1 wt % or less. If the content of the structural unit derived from the aromatic vinyl compound in the polymer block [A] is too low, the heat resistance of the medical formed article may deteriorate.

A plurality of polymer blocks [A] may be either identical or different as long as the above range is satisfied.

The polymer block [B] includes a structural unit (repeating unit) derived from a linear conjugated diene compound as the main component. The content of the structural unit derived from the linear conjugated diene compound in the polymer block [B] is normally 50 wt % or more, preferably 70 wt % or more, and more preferably 90 wt % or more. When the content of the structural unit derived from the linear conjugated diene compound is within the above range, the resin composition exhibits flexibility and fusibility (high-frequency fusibility and heat fusibility) in a well-balanced manner.

The polymer block [B] may include a component other than the structural unit derived from the linear conjugated diene compound. Examples of the component other than the structural unit derived from the linear conjugated diene compound include a structural unit derived from an aromatic vinyl compound and/or a structural unit derived from an additional vinyl compound. The content of the component other than the structural unit derived from the linear conjugated diene compound in the polymer block [B] is normally 30 wt % or less, and preferably 10 wt % or less. The transparency of the medical formed article is improved as the content of a structural unit derived from an aromatic vinyl compound in the polymer block [B] increases. If the content of a structural unit derived from an aromatic vinyl compound is too high, however, the medical formed article may exhibit poor flexibility and poor fusibility (high-frequency fusibility and heat fusibility).

When the block copolymer (C) includes a plurality of polymer blocks [B], the plurality of polymer blocks [B] may be either identical or different as long as the above range is satisfied.

Examples of the aromatic vinyl compound used in connection with the embodiments of the invention include styrene; an alkyl-substituted styrene such as α-methylstyrene, 2-methylstyrene, 3-methylstyrene, 4-methylstyrene, 2,4-diisopropylstyrene, 2,4-dimethylstyrene, 4-t-butylstyrene, and 5-t-butyl-2-methylstyrene; a halogen-substituted styrene such as 4-chlorostyrene and 2,4-dichlorostyrene; and the like. Among these, styrene is particularly preferable from the viewpoint of industrial availability.

Examples of the linear conjugated diene compound used in connection with the embodiments of the invention include 1,3-butadiene, isoprene, 2,3-dimethyl-1,3-butadiene, 1,3-pentadiene, and the like. Among these, 1,3-butadiene and isoprene are particularly preferable from the viewpoint of industrial availability and ease of polymerization control.

Examples of the additional vinyl compound that may be used in connection with the embodiments of the invention include a linear vinyl compound and a cyclic vinyl compound. A vinyl compound that does not include a polar group (e.g., a linear olefin such as ethylene, propylene, 1-butene, 1-pentene, 1-hexene, 1-heptene, 1-octene, 1-nonene, 1-decene, 1-dodecene, 1-eicosene, 4-methyl-1-pentene, and 4,6-dimethyl-1-heptene; and a cyclic olefin such as vinylcyclohexane) is preferable as the additional vinyl compound from the viewpoint of acid resistance and alkali resistance. A linear olefin is more preferable, and ethylene and propylene are particularly preferable as the additional vinyl compound.

The number of polymer blocks [A] included in the block copolymer (C) is normally 5 or less, preferably 4 or less, and more preferably 3 or less.

When the block copolymer (C) includes a plurality of polymer blocks [A] and/or a plurality of polymer blocks [B], the ratio (Mw(A1)/Mw(A2)) of the weight average molecular weight Mw(A1) of the polymer block among the plurality of polymer blocks [A] that has the highest weight average molecular weight to the weight average molecular weight Mw(A2) of the polymer block among the plurality of polymer blocks [A] that has the lowest weight average molecular weight, and the ratio (Mw(B1)/Mw(B2)) of the weight average molecular weight Mw(B1) of the polymer block among the plurality of polymer blocks [B] that has the highest weight average molecular weight to the weight average molecular weight Mw(B2) of the polymer block among the plurality of polymer blocks [B] that has the lowest weight average molecular weight, are normally 2.0 or less, preferably 1.5 or less, and more preferably 1.2 or less.

The block copolymer (C) may be a linear block copolymer or a radial block copolymer. It is preferable that the block copolymer (C) be a linear block copolymer since excellent mechanical strength can be obtained.

It is most preferable that the block copolymer (C) be a triblock copolymer [A]-[B]-[A]) in which the polymer block [A] is bonded to each end of the polymer block [B], or a pentablock copolymer [A]-[B]-[A]-[B]-[A]) in which the polymer block [B] is bonded to each end of the polymer block [A], and the polymer block [A] is bonded to the other end of each polymer block [B].

The ratio (wA:wB) of the weight fraction wA of the polymer block [A] in the block copolymer (C) to the weight fraction wB of the polymer block [B] in the block copolymer (C) is 30:70 to 70:30, preferably 35:65 to 65:35, and more preferably 40:60 to 60:40. If the weight fraction wA is too high, a decrease in flexibility and impact resistance may occur, although the heat resistance of the resin composition increases. If the weight fraction wA is too low, significant deformation may occur during steam sterilization due to a decrease in heat resistance.

The polystyrene-equivalent weight average molecular weight (Mw) of the block copolymer (C) measured by GPC using tetrahydrofuran (THF) as an eluent is normally 30,000 to 150,000, preferably 40,000 to 130,000, and more preferably 50,000 to 100,000. The molecular weight distribution (Mw/Mn) of the block copolymer (C) is preferably 3 or less, more preferably 2 or less, and particularly preferably 1.5 or less.

The block copolymer (C) may be produced using a method that alternately polymerizes a monomer mixture (a) that includes the aromatic vinyl compound as the main component, and a monomer mixture (b) that includes the linear conjugated diene compound as the main component, through living anionic polymerization or the like; or a method that sequentially polymerizes a monomer mixture (a) that includes the aromatic vinyl compound as the main component, and a monomer mixture (b) that includes the linear conjugated diene compound as the main component, and couples the terminals of the resulting polymer block [B] using a coupling agent, for example.

2. Hydrogenated Block Copolymer [1]

The hydrogenated block copolymer [1] used in connection with the embodiments of the invention is obtained by hydrogenating the carbon-carbon unsaturated bonds of the main chain, the side chain, and the aromatic ring of the block copolymer (C). The hydrogenation rate of the hydrogenated block copolymer [1] is normally 99% or more, preferably 99.5% or more, and more preferably 99.9% or more. If the hydrogenation rate is less than 99%, it may be difficult to suppress a situation in which a significant change in pH due to elution (from the medical formed article) in water occurs as a result of the sterilization process that applies high-energy rays.

The hydrogenation rate of the hydrogenated block copolymer may be determined by $^1$H-NMR analysis, or may be determined by comparing the peak areas detected by a UV detector and an RI detector through gel permeation chromatography (GPC), for example.

The unsaturated bond hydrogenation method, the reaction method, and the like are not particularly limited. The unsaturated bonds may be hydrogenated using a known method. It is preferable to use a hydrogenation method that can increase the hydrogenation rate, and causes a polymer chain cleavage reaction to only a small extent. Examples of such a hydrogenation method include the methods disclosed in WO2011/096389, WO2012/043708, and the like.

After removing a hydrogenation catalyst and/or a polymerization catalyst from the reaction solution including the hydrogenated block copolymer, the hydrogenated block copolymer [1] is collected from the reaction solution. The hydrogenated block copolymer thus collected may normally be pelletized, and formed to produce a medical formed article, for example.

The polystyrene-equivalent weight average molecular weight (Mw) of the hydrogenated block copolymer [1] measured by gel permeation chromatography (GPC) using THF as an eluent is normally 30,000 to 150,000, preferably 40,000 to 130,000, and more preferably 50,000 to 100,000. The molecular weight distribution (Mw/Mn) of the hydrogenated block copolymer [1] is preferably 3 or less, more preferably 2 or less, and particularly preferably 1.5 or less. When the weight average molecular weight (Mw) and the molecular weight distribution (Mw/Mn) of the hydrogenated block copolymer [1] are within the above ranges, the mechanical strength and the heat resistance of the resulting medical formed article are improved.

3. Antioxidant

It is preferable to use the phenol-based antioxidant in combination with the hydrogenated block copolymer [1] used in connection with the embodiments of the invention in order to suppress a situation in which a significant change in pH due to elution in water occurs as a result of the sterilization process that applies high-energy rays to the medical formed article. The phenol-based antioxidant can advantageously suppress a situation in which a significant change in pH due to elution in water occurs as a result of the sterilization process that applies high-energy rays.

The phenol-based antioxidant is used in such an amount that, when the hydrogenated block copolymer [1] is melted and formed to produce a medical formed article, and the medical formed article is sterilized by applying high-energy rays, it is possible to suppress a situation in which a significant change in pH occurs due to elution in water, suppress a decrease in the transparency of the medical formed article, and suppress a bleed-out phenomenon during long-term storage. The phenol-based antioxidant is used in a ratio of W to 0.50 parts by weight based on 100 parts by weight of the hydrogenated block copolymer [1], W being calculated by the following expression (1).

$$W=[0.46\times(100-H)+0.04]\times(E/25) \qquad (1)$$

where, W is the ratio (parts by weight) of the phenol-based antioxidant based on 100 parts by weight of the hydrogenated block copolymer [1], H is the hydrogenation rate (%) of the hydrogenated block copolymer [1], H is a numerical value from 99 to 100, and E is the exposure (kGy) of the high-energy rays.

The phenol-based antioxidant is added in such an amount that it is possible to prevent the oxidation of the carbon-carbon double bonds and the carbon-carbon single bonds. "0.46×(100−H)" in the expression (1) corresponds to the amount of the antioxidant required to prevent the oxidation of the carbon-carbon double bonds when energy rays are applied at an exposure of 25 kGy, and "0.04" in the expression (1) corresponds to the amount of the antioxidant required to prevent the oxidation of the carbon-carbon single bonds when energy rays are applied at an exposure of 25 kGy.

Since the degree of oxidation varies depending on the exposure of the high-energy rays, it is necessary to multiply "[0.46×(100−H)+0.04]" by "(E/25)" as a coefficient that corresponds to the actual exposure based on 25 kGy.

If the ratio (amount) of the antioxidant is less than W parts by weight (calculated by the expression (1)), it may be difficult to suppress a situation in which a significant change in pH due to elution in water occurs as a result of sterilizing the formed article by applying high-energy rays. If the ratio (amount) of the antioxidant exceeds 0.50 parts by weight, a bleed-out phenomenon may easily occur when the formed article is stored for a long time.

Specific examples of the phenol-based antioxidant include pentaerythrityl-tetrakis[3-(3,5-di-t-butyl-4-hydroxyphenyl) propionate], 1,3,5-tris(3,5-di-t-butyl-4-hydroxybenzyl)-1,3,5-triazine-2,4,6-(1H,3H,5H)-trione, 1,3,5-tris(3,5-di-t-butyl-4-hydroxyphenylmethyl)-2,4,6-trimethylbenzene, 3,9-bis{2-[3-(3-t-butyl-4-hydroxy-5-methylphenyl)propionyloxy]-1,1-dimethylethyl}-2,4,8,10-tetraoxaspiro[5.5]undecane, octadecyl-3-(3,5-di-t-butyl-4-hydroxyphenyl) propionate, 2,2'-thiodiethylenebis[3-(3,5-di-t-butyl-4-hydroxyphenyl) propionate], 6,6'-di-t-butyl-4,4'-butylidenedi-m-cresol, 4,4'-butylidenebis-(6-t-butyl-3-methylphenol), 2,2'-methylenebis(4-ethyl-6-t-butylphenol), and the like. It is preferable to use a phenol-based antioxidant having a molecular weight of 500 or more since a bleed-out phenomenon from the resin composition rarely occurs.

4. Medical Formed Article

The medical formed article (hereinafter may be referred to as "medical formed article [3]") used in connection with the embodiments of the invention is obtained by forming (molding) the resin composition [2] that includes the hydrogenated block copolymer [1] and a specific amount of the phenol-based antioxidant. The medical formed article [3] exhibits excellent transparency, heat resistance, flexibility, mechanical strength, and the like, and does not show a change in external appearance (e.g., change in transparency and coloration) (i.e., can maintain excellent content visibility) even after being sterilized by applying high-energy rays.

The medical formed article [3] used in connection with the embodiments of the invention may be obtained by forming (molding) the resin composition [2] in the shape of a container, a tube, a sheet, or the like using a melt extrusion molding method, an injection molding method, an injection blow molding method, a blow molding method, an inflation molding method, or the like.

When the resin composition [2] is formed in the shape of a sheet, the sheet may be cut to have the desired shape, and bonded by high-frequency fusion or heat fusion to form a bag or a bag-like container.

The resin composition [2] is formed (molded) under conditions that are appropriately selected taking account of the forming (molding) method. For example, when using a melt extrusion molding method, an injection molding method, or the like, the molten resin temperature is normally selected within the range from 170 to 260° C., preferably 180 to 240° C., and more preferably 190 to 220° C.

If the molten resin temperature is too low, it may be difficult to obtain a formed article having a good shape due to a decrease in fluidity. If the resin temperature is too high, a significant change in pH may occur due to elution (from the medical formed article [3]) in water, or a decrease in mechanical strength may occur.

5. Sterilization Process that Applies High-Energy Rays

The method for producing a sterilized medical formed article according to one embodiment of the invention includes applying high-energy rays to the medical formed article [3] obtained as described above at the exposure E.

It is preferable to apply high-energy rays to the medical formed article [3] in a state in which the medical formed article [3] is contained in an airtight container that is formed of a resin film that does not allow bacteria to pass through in order to maintain sterility. The sterilized medical formed article [3] is stored in the airtight container formed of the resin film before use while maintaining sterility.

For example, the medical formed article [3] is put in a resin bag (e.g., polyethylene bag), and the opening of the resin bag is sealed using a heat seal method or the like. After packing the sealed bag in a resin film bag or the like, the resin film bag or the like is packed in a cardboard box or a plastic case used for transportation, and the sterilization process is performed by applying high-energy rays.

The airtight container formed of the resin film in which the medical formed article [3] is placed when performing the sterilization process by applying high-energy rays may be a single-layer or multi-layer bag or case that is formed of a resin. Examples of the resin include an ethylene-vinyl alcohol copolymer, low-density polyethylene, high-density polyethylene, linear low-density polyethylene, polypropylene, an ethylene-propylene copolymer, a polycarbonate, polystyrene, polyvinyl chloride, polyvinylidene chloride, polyethylene terephthalate, polybutylene terephthalate, polyamide-6, polyamide-66, -polyamide-12, and the like. These resins may be used either alone or in combination.

The opening of the resin bag or the like in which the medical formed article [3] is placed may be sealed using a heat seal method or the like.

For example, when a film that is formed of an ethylene-vinyl alcohol copolymer, polyethylene terephthalate, polyamide-6, or the like and has an oxygen transmission rate of 100 cc/m$^2$·day·atm or less is used as the resin film that forms the airtight container, and the sterilization process is performed by applying high-energy rays in a state in which the oxygen concentration in the airtight container is reduced by placing a deoxidant in the airtight container in which the medical formed article [3] is placed, a change in pH due to elution (from the sterilized medical formed article) in water is further reduced or suppressed.

Examples of the high-energy rays that can be used in connection with the embodiments of the invention include X-rays, γ-rays, β-rays, electron beams, neutron rays, and the like. It is particularly preferable to perform the sterilization process by applying γ-rays or electron beams.

It is preferable to sterilize the medical formed article [3] by applying the high-energy rays at an exposure of 20 to 35 kGy. If the exposure is less than 20 kGy, a sufficient sterilization effect may not be obtained. If the exposure exceeds 35 kGy, the application of the high-energy rays may take time, and elution from the sterilized medical formed article [3] (that is formed of the hydrogenated block copolymer) may increase.

Examples of the sterilized medical formed article [3] produced using the production method according to one embodiment of the invention include a liquid, powder, or solid medicine container such as an injection liquid container, an ampoule, an infusion bag, a solid medicine container, an eye drop container, a drip container, a test drug container, and a nutrient preparation container; a sample container such as a blood sampling tube, a blood collection tube, and a sample container; a tube material such as an infusion tube, a pipe, a joint, a valve, and a cock; a contact lens storage container; an artificial internal organ such as a denture base, an artificial heart, and an artificial kidney, or a part thereof; and the like. Among these, an infusion bag, a nutrient preparation container, a medicine bottle, an ampoule, and the like that are used to store a medicine (particularly a liquid medicine) for a long time are particularly preferable since the amount of elution from the container can be reduced.

EXAMPLES

The invention is further described below by way of examples and comparative examples. Note that the invention is not limited to the following examples. In the examples and the comparative examples, the unit "parts" refers to "parts by weight", and the unit "%" refers to "wt %", unless otherwise indicated.

The following property measurement methods were used in the examples and the comparative examples.

(1) Weight Average Molecular Weight (Mw) and Molecular Weight Distribution (Mw/Mn)

The molecular weight (standard polystyrene-equivalent value) of the block copolymer and the hydrogenated block copolymer was measured at 38° C. by gel permeation chromatography (GPC) using THF as an eluent. The molecular weight was measured using a system "HLC-8020 GPC" manufactured by Tosoh Corporation.

(2) Hydrogenation Rate

The hydrogenation rate of the hydrogenated block copolymer refers to the ratio of the number of hydrogenated carbon-carbon bonds to the total number of carbon-carbon unsaturated bonds of the aromatic ring of the structural unit derived from the aromatic vinyl compound included in the block copolymer (precursor), and carbon-carbon unsaturated bonds of the structural unit derived from the linear conjugated diene compound included in the block copolymer (precursor).

The hydrogenation rate of the hydrogenated block copolymer was calculated from the $^1$H-NMR spectrum, or calculated by GPC analysis.

Specifically, a hydrogenation rate equal to or less than 99% or less was calculated from the $^1$H-NMR spectrum, and a hydrogenation rate exceeding 99% was calculated from the ratio of the peak areas detected by a UV detector and an RI detector through GPC.

(3) Elution Test

The pellets of the resin composition including the hydrogenated block copolymer and the antioxidant were subjected to injection blow molding to produce a single-layer vial having a diameter of 50 mm, a height of 90 mm, and a sidewall thickness of 1 mm. The vial was sterilized by applying γ-rays at an exposure of 25 or 35 kGy. A sample (length: 60 mm, width: 10 mm) cut from the side of the vial before applying γ-rays and a sample (length: 60 mm, width: 10 mm) cut from the side of the vial after applying γ-rays were subjected to an elution test in accordance with the Japanese Pharmacopoeia 16th Edition (see "Test Methods for Plastic Containers") to evaluate the difference in pH, foaming, UV absorption, and a potassium permanganate-reducing substance.

The following evaluation criteria were used. The evaluation results are shown in Table 2.

Change in pH: A case where the difference in pH with respect to a blank sample was within ±1.0 was evaluated as "Good", and a case where the difference in pH with respect to the blank sample was not within ±1.0 was evaluated as "Bad".

Foaming: A case where defoaming occurred within 3 minutes was evaluated as "Good", and a case where defoaming did not occur within 3 minutes was evaluated as "Bad".

UV absorption: A case where the difference in absorbance at 220 to 241 nm with respect to the blank sample was 0.08 or less was evaluated as "Good", and a case where the difference in absorbance at 220 to 241 nm with respect to the blank sample was more than 0.08 was evaluated as "Bad". A case where the difference in absorbance at 241 to 350 nm with respect to the blank sample was 0.05 or less was evaluated as "Good", and a case where the difference in absorbance at 241 to 350 nm with respect to the blank sample was more than 0.05 was evaluated as "Bad".

Amount of potassium permanganate-reducing substance: A case where the difference in consumption of a 0.002 mol/L potassium permanganate solution was 1.0 mL or less was evaluated as "Good", and a case where the difference in consumption of a 0.002 mol/L potassium permanganate solution was more than 1.0 mL was evaluated as "Bad".

(4) Bleed-Out Phenomenon Test

The surface of the vial obtained by injection blow molding (see above) was observed with the naked eye, and the IR spectrum of the inner part of the wall of the vial and the IR spectrum of the surface of the vial were measured (over time) using an attenuated total reflection (ATR) method. The intensity of the absorption band attributed to the hydrogenated block copolymer and the intensity of the absorption band attributed to the antioxidant were measured and compared to determine whether or not a bleed-out phenomenon occurred.

It was determined that a bleed-out phenomenon occurred when the intensity of the absorption band attributed to the antioxidant in the IR spectrum of the surface of the vial was higher than that of the IR spectrum of the inner part of the vial by a factor of 1.5 (when 30 days had elapsed after production).

In Table 2, a case where a bleed-out phenomenon did not occur is indicated by "Good", and a case where a bleed-out phenomenon occurred is indicated by "Bad".

Reference Example 1

Preparation of Resin Composition [2]-1 Including Hydrogenated Block Copolymer and Antioxidant A reactor equipped with a stirrer in which the internal atmosphere had been sufficiently replaced with nitrogen, was charged with 550 parts of dehydrated cyclohexane, 25.0 parts of dehydrated styrene, and 0.475 parts of n-dibutyl ether. 0.67 parts of n-butyllithium (15% cyclohexane solution) was added to the mixture at 60° C. with stirring to initiate polymerization, and the mixture was reacted at 60° C. for 60 minutes with stirring. The polymerization conversion ratio determined by subjecting the reaction mixture to gas chromatography was 99.5%.

After the addition of 50.0 parts of dehydrated isoprene to the reaction mixture, the resulting mixture was stirred at 60° C. for 30 minutes. The polymerization conversion ratio determined by subjecting the reaction mixture to gas chromatography was 99%.

After the addition of 25.0 parts of dehydrated styrene to the reaction mixture, the resulting mixture was stirred at 60° C. for 60 minutes. The polymerization conversion ratio determined by subjecting the reaction mixture to gas chromatography was about 100%.

0.5 parts of isopropyl alcohol was then added to the reaction mixture to terminate the reaction. The resulting block copolymer [C]-1 had a weight average molecular weight (Mw) of 62,600 and a molecular weight distribution (Mw/Mn) of 1.05.

The polymer solution was transferred to a pressure-resistant reactor equipped with a stirrer. After the addition of 4.0 parts of a nickel catalyst supported on diatomaceous earth ("E22U" manufactured by JGC Catalysts and Chemicals Ltd., nickel content (amount of nickel supported): 60%) (hydrogenation catalyst) and 100 parts of dehydrated cyclohexane, the mixture was mixed. After replacing the atmosphere inside the reactor with hydrogen gas, hydrogen was supplied to the reactor while stirring the solution to effect a hydrogenation reaction at a temperature of 170° C. for 6 hours under a pressure of 4.5 MPa.

The resulting hydrogenated block copolymer [1]-1 had a weight average molecular weight (Mw) of 66,200 and a molecular weight distribution (Mw/Mn) of 1.06.

After completion of the hydrogenation reaction, the hydrogenation catalyst was removed by filtering the reaction mixture, and 1.0 part of a solution prepared by dissolving 0.05 parts of pentaerythrityl-tetrakis[3-(3,5-di-t-butyl-4-hydroxyphenyl) propionate] ("Irganox (registered trademark) 1010" manufactured by BASF) (phenol-based antioxidant) in xylene was added to (dissolved in) the filtrate.

After filtering the solution sequentially through a Zeta Plus (registered trademark) filter 30H (manufactured by Cuno, pore size: 0.5 to 1 μm) and a metal fiber filter (manufactured by Nichidai Corporation, pore size: 0.4 μm) to remove microscopic solids, the solvent (cyclohexane and xylene) and other volatile components were removed from the solution at a temperature of 260° C. under a pressure of 0.001 MPa or less using a cylindrical evaporator (manufactured by Hitachi Ltd.). The residue was extruded in the shape of a strand in a molten state from a die directly connected to the evaporator, cooled, and cut using a pelletizer to obtain 94 parts of pellets of a resin composition [2]-1 including the hydrogenated block copolymer [1]-1 and the antioxidant.

The hydrogenated block copolymer [1]-1 included in the resin composition [2]-1 had a weight average molecular weight (Mw) of 65,600 and a molecular weight distribution (Mw/Mn) of 1.11. The hydrogenation rate was 99.9%, and the ratio "wA:wB" was 50:50. The resin composition [2]-1 included the antioxidant in a ratio of 0.05 parts by weight based on 100 parts by weight of the hydrogenated block copolymer [1]-1. Table 1 shows the resulting data.

Reference Example 2

Preparation of Resin Composition [2]-2 Including Hydrogenated Block Copolymer and Antioxidant 94 parts of pellets of a resin composition [2]-2 including a hydrogenated block copolymer [1]-2 and an antioxidant were obtained in the same manner as in Reference Example 1, except that 3.5 parts of the hydrogenation catalyst was used.

The hydrogenated block copolymer [1]-2 included in the resin composition [2]-2 had a weight average molecular weight (Mw) of 65,100 and a molecular weight distribution (Mw/Mn) of 1.11. The hydrogenation rate was 99.6%, and the ratio "wA:wB" was 50:50. The resin composition [2]-2 included the antioxidant in a ratio of 0.05 parts by weight based on 100 parts by weight of the hydrogenated block copolymer [1]-2. Table 1 shows the resulting data.

Reference Example 3

Preparation of Resin Composition [2]-3 Including Hydrogenated Block Copolymer and Antioxidant 95 parts of pellets of a resin composition [2]-3 including a hydrogenated block copolymer [1]-3 and an antioxidant were obtained in the same manner as in Reference Example 1, except that 20.0 parts of styrene, 0.54 parts of n-butyllithium (15% cyclohexane solution), 60.0 parts of isoprene, and 20.0 parts of styrene were sequentially added to the reaction system and polymerized, and 5.0 parts of the hydrogenation catalyst was used.

The hydrogenated block copolymer [1]-3 included in the resin composition [2]-3 had a weight average molecular weight (Mw) of 81,000 and a molecular weight distribution (Mw/Mn) of 1.15. The hydrogenation rate was 99.2%, and the ratio "wA:wB" was 40:60. The resin composition [2]-3 included the antioxidant in a ratio of 0.05 parts by weight based on 100 parts by weight of the hydrogenated block copolymer [1]-3. Table 1 shows the resulting data.

Reference Example 4

Preparation of Resin Composition [2]-4 Including Hydrogenated Block Copolymer and Antioxidant 92 parts of pellets of a resin composition [2]-4 including a hydrogenated block copolymer [1]-4 and an antioxidant were obtained in the same manner as in Reference Example 1, except that 0.53 parts of n-butyllithium (15% cyclohexane solution) was added.

The hydrogenated block copolymer [1]-4 included in the resin composition [2]-4 had a weight average molecular weight (Mw) of 82,900 and a molecular weight distribution (Mw/Mn) of 1.16. The hydrogenation rate was 98.1%, and the ratio "wA:wB" was 50:50. The resin composition [2]-4 included the antioxidant in a ratio of 0.05 parts by weight based on 100 parts by weight of the hydrogenated block copolymer [1]-4. Table 1 shows the resulting data.

Reference Example 5

Preparation of Resin Composition [2]-1MP Including Hydrogenated Block Copolymer and Antioxidant 0.96 parts by weight of pentaerythrityl-tetrakis[3-(3,5-di-t-butyl-4-hydroxyphenyl) propionate] was added to 100 parts by weight of the pellets of the resin composition [2]-1 including the hydrogenated block copolymer [1]-1 and the antioxidant (prepared in Reference Example 1), and the mixture was kneaded at a resin temperature of 230° C. using a twin-screw kneader ("TEM37BS" manufactured by Toshiba Machine Co., Ltd.), extruded in the shape of a strand, and cut using a pelletizer to obtain 97 parts of pellets of a resin composition [2]-1MP including the hydrogenated block copolymer and the antioxidant.

The resin composition [2]-1MP included the antioxidant in a ratio of 1.00 part by weight based on 100 parts by weight of the hydrogenated block copolymer [1]-1. Table 1 shows the data (i.e., the ratio "wA:wB", the weight average molecular weight (Mw), the hydrogenation rate, and the ratio of the antioxidant) for the resin composition [2]-1MP.

Reference Example 6

Preparation of Resin Composition [2]-2MP Including Hydrogenated Block Copolymer and Antioxidant 0.96 parts by weight of pentaerythrityl-tetrakis[3-(3,5-di-t-butyl-4-hydroxyphenyl) propionate] was added to 100 parts by weight of the pellets of the resin composition [2]-2 including the hydrogenated block copolymer [1]-2 and the antioxidant (prepared in Reference Example 2), and the mixture was processed in the same manner as in Reference Example 5 to obtain 98 parts of pellets of a resin composition [2]-2MP including the hydrogenated block copolymer [1]-2 and the antioxidant.

The resin composition [2]-2MP included the antioxidant in a ratio of 1.00 part by weight based on 100 parts by weight of the hydrogenated block copolymer [1]-2. Table 1 shows the data (i.e., the ratio "wA:wB", the weight average molecular weight (Mw), the hydrogenation rate, and the ratio of the antioxidant) for the resin composition [2]-2MP.

Reference Example 7

Preparation of Resin Composition [2]-3MP Including Hydrogenated Block Copolymer and Antioxidant 0.96 parts by weight of pentaerythrityl-tetrakis[3-(3,5-di-t-butyl-4-hydroxyphenyl) propionate] was added to 100 parts by weight of the pellets of the resin composition [2]-3 including the hydrogenated block copolymer [1]-3 and the antioxidant (prepared in Reference Example 3), and the mixture was processed in the same manner as in Reference Example 5 to obtain 97 parts of pellets of a resin composition [2]-3MP including the hydrogenated block copolymer [1]-3 and the antioxidant.

The resin composition [2]-3MP included the antioxidant in a ratio of 1.00 part by weight based on 100 parts by weight of the hydrogenated block copolymer [1]-3. Table 1 shows the data (i.e., the ratio "wA:wB", the weight average molecular weight (Mw), the hydrogenation rate, and the ratio of the antioxidant) for the resin composition [2]-3MP.

Reference Example 8

Preparation of Resin Composition [2]-4MP Including Hydrogenated Block Copolymer and Antioxidant 0.96 parts by weight of pentaerythrityl-tetrakis[3-(3,5-di-t-butyl-4-hydroxyphenyl) propionate] was added to 100 parts by weight of the pellets of the resin composition [2]-4 including the hydrogenated block copolymer [1]-4 and the antioxidant (prepared in Reference Example 4), and the mixture was processed in the same manner as in Reference Example 5 to obtain 96 parts of pellets of a resin composition [2]-4MP including the hydrogenated block copolymer [1]-4 and the antioxidant. The resin composition [2]-4MP included the antioxidant in a ratio of 1.00 part by weight based on 100 parts by weight of the hydrogenated block copolymer [1]-4. Table 1 shows the data (i.e., the ratio "wA:wB", the weight average molecular weight (Mw), the hydrogenation rate, and the ratio of the antioxidant) for the resin composition [2]-4MP.

TABLE 1

| | Hydrogenated block copolymer | | | | |
| --- | --- | --- | --- | --- | --- |
| | Resin composition | wA:wB | Mw | Hydrogenation rate (%) | Anti-oxidant[*1)] |
| Reference Example 1 | [2]-1 | 50:50 | 65,600 | 99.9 | 0.05 |
| Reference Example 2 | [2]-2 | 50:50 | 65,100 | 99.6 | 0.05 |
| Reference Example 3 | [2]-3 | 40:60 | 81,000 | 99.2 | 0.05 |
| Reference Example 4 | [2]-4 | 50:50 | 82,900 | 98.1 | 0.05 |
| Reference Example 5 | [2]-1MP | 50:50 | 65,600 | 99.9 | 1.00 |
| Reference Example 6 | [2]-2MP | 50:50 | 65,100 | 99.6 | 1.00 |
| Reference Example 7 | [2]-3MP | 40:60 | 81,000 | 99.2 | 1.00 |
| Reference Example 8 | [2]-4MP | 50:50 | 82,900 | 98.1 | 1.00 |

[*1)]Antioxidant (parts by weight)/hydrogenated block copolymer (100 parts by weight)

Example 1

95 parts by weight of the pellets of the resin composition [2]-1 obtained in Reference Example 1 and 5 parts of the pellets of the resin composition [2]-1MP obtained in Reference Example 5 were homogenously mixed using a blender. The mixed pellets included the antioxidant in a ratio of 0.098 parts by weight based on 100 parts by weight of the hydrogenated block copolymer [1]-1.

The mixed pellets were injection-molded using an injection blow molding machine ("ASB-50 MB" manufactured by Nissei ASB Machine Co., Ltd.) (cylinder temperature: 240° C., injection mold temperature: 60° C.) to produce a preform. The preform was blow-molded (heating pot temperature: 150° C., blow pressure: 0.5 MPa, blow mold temperature: 60° C.) to produce a single-layer vial having a diameter of 50 mm, a height of 90 mm, and a sidewall thickness of 1 mm. The resulting vial was colorless and transparent, and exhibited excellent content visibility.

Ten vials produced as described above were put in a bag (length: 35 cm, width: 25 cm, thickness: 0.05 mm) made of linear low-density polyethylene (LLDPE), and the bag was sealed using a heat seal method. The sealed bag was packed in a bag (45 L) made of linear low-density polyethylene (LLDPE), which was packed in a cardboard box. Note that a plurality of bags were packed in the cardboard box. The vials were sterilized by applying γ-rays (exposure: 25 kGy, Koga Isotope, Ltd.) in a state in which the vials were packed in the cardboard box.

In Example 1, the value W (i.e., the lower limit of the amount of the antioxidant) calculated by the expression (1) is 0.086.

The cardboard box was opened when 5 days had elapsed after applying γ-rays, and the vials were removed. The vials were colorless and transparent, and no change in external appearance was observed. A specific amount of sample was cut from the vial sterilized by applying γ-rays and the unsterilized vial, and subjected to an elution test in accordance with the Japanese Pharmacopoeia 16th Edition (see "Test Methods for Plastic Containers"). The results are shown in Table 2.

The surface of the vial that was sealed in a polyethylene bag and stored at room temperature for 30 days was observed with the naked eye, and the IR spectrum of the surface of the vial was measured. The intensity of the absorption band (2930 $cm^{-1}$) attributed to the hydrogenated block copolymer ([1]-1 to [1]-4) and the intensity of the absorption band (1740 $cm^{-1}$) attributed to the antioxidant were compared to determine whether or not a bleed-out phenomenon occurred. The results are shown in Table 2.

Comparative Example 1

The sterilization process (that applies γ-rays), the elution test, and the bleed-out phenomenon test were performed in the same manner as in Example 1, except that 100 parts by weight of the pellets of the resin composition [2]-1 obtained in Reference Example 1 (including the antioxidant in a ratio of 0.05 parts by weight based on 100 parts by weight of the hydrogenated block copolymer [1]-1) were used. The results are shown in Table 2.

Comparative Example 2

The sterilization process (that applies γ-rays), the elution test, and the bleed-out phenomenon test were performed in the same manner as in Example 1, except that 50 parts by weight of the pellets of the resin composition [2]-1 obtained in Reference Example 1 and 50 parts by weight of the pellets of the resin composition [2]-1MP obtained in Reference Example 5 were mixed so that the mixed pellets included the antioxidant in a ratio of 0.525 parts by weight based on 100 parts by weight of the hydrogenated block copolymer [1]-1. The results are shown in Table 2.

Example 2

The sterilization process (that applies γ-rays), the elution test, and the bleed-out phenomenon test were performed in the same manner as in Example 1, except that 77 parts by weight of the pellets of the resin composition [2]-2 obtained in Reference Example 2 and 23 parts by weight of the pellets of the resin composition [2]-2MP obtained in Reference Example 6 were mixed so that the mixed pellets included the antioxidant in a ratio of 0.269 parts by weight based on 100 parts by weight of the hydrogenated block copolymer [1]-2. The results are shown in Table 2.

Comparative Example 3

The sterilization process (that applies γ-rays), the elution test, and the bleed-out phenomenon test were performed in the same manner as in Example 1, except that 90 parts by weight of the pellets of the resin composition [2]-2 obtained in Reference Example 2 and 10 parts by weight of the pellets of the resin composition [2]-2MP obtained in Reference Example 6 were mixed so that the mixed pellets included the antioxidant in a ratio of 0.145 parts by weight based on 100 parts by weight of the hydrogenated block copolymer [1]-2. The results are shown in Table 2.

Example 3

The sterilization process (that applies γ-rays), the elution test, and the bleed-out phenomenon test were performed in the same manner as in Example 1, except that 58 parts by weight of the pellets of the resin composition [2]-3 obtained in Reference Example 3 and 42 parts by weight of the pellets of the resin composition [2]-3MP obtained in Reference Example 7 were mixed so that the mixed pellets included the antioxidant in a ratio of 0.449 parts by weight based on 100 parts by weight of the hydrogenated block copolymer [1]-3. The results are shown in Table 2.

Comparative Example 4

The sterilization process (that applies γ-rays), the elution test, and the bleed-out phenomenon test were performed in the same manner as in Example 1, except that 73 parts by weight of the pellets of the resin composition [2]-3 obtained in Reference Example 3 and 27 parts by weight of the pellets of the resin composition [2]-3MP obtained in Reference Example 7 were mixed so that the mixed pellets included the antioxidant in a ratio of 0.307 parts by weight based on 100 parts by weight of the hydrogenated block copolymer [1]-3. The results are shown in Table 2.

Comparative Example 5

The sterilization process (that applies γ-rays), the elution test, and the bleed-out phenomenon test were performed in the same manner as in Example 1, except that 50 parts by weight of the pellets of the resin composition [2]-3 obtained in Reference Example 3 and 50 parts by weight of the pellets of the resin composition [2]-3MP obtained in Reference Example 7 were mixed so that the mixed pellets included the antioxidant in a ratio of 0.525 parts by weight based on 100 parts by weight of the hydrogenated block copolymer [1]-3. The results are shown in Table 2.

Comparative Example 6

The sterilization process (that applies γ-rays), the elution test, and the bleed-out phenomenon test were performed in the same manner as in Example 1, except that 47 parts by weight of the pellets of the resin composition [2]-4 obtained in Reference Example 4 and 53 parts by weight of the pellets of the resin composition [2]-4MP obtained in Reference Example 8 were mixed so that the mixed pellets included the antioxidant in a ratio of 0.554 parts by weight based on 100 parts by weight of the hydrogenated block copolymer [1]-4. The results are shown in Table 2.

Example 4

The sterilization process (that applies γ-rays), the elution test, and the bleed-out phenomenon test were performed in the same manner as in Example 1, except that 85 parts by weight of the pellets of the resin composition [2]-1 obtained in Reference Example 1 and 15 parts by weight of the pellets of the resin composition [2]-1MP obtained in Reference Example 5 were mixed so that the mixed pellets included the antioxidant in a ratio of 0.193 parts by weight based on 100 parts by weight of the hydrogenated block copolymer [1]-1, and the exposure was changed to 35 kGy. The results are shown in Table 2.

Comparative Example 7

The sterilization process (that applies γ-rays), the elution test, and the bleed-out phenomenon test were performed in the same manner as in Example 1, except that the vials produced in Example 1 were used, and the exposure was changed to 35 kGy. The results are shown in Table 2.

Example 5

The sterilization process (that applies γ-rays), the elution test, and the bleed-out phenomenon test were performed in the same manner as in Example 1, except that 65 parts by weight of the pellets of the resin composition [2]-2 obtained in Reference Example 2 and 35 parts by weight of the pellets of the resin composition [2]-2MP obtained in Reference Example 6 were mixed so that the mixed pellets included the antioxidant in a ratio of 0.383 parts by weight based on 100 parts by weight of the hydrogenated block copolymer [1]-2, and the exposure was changed to 35 kGy. The results are shown in Table 2.

Comparative Example 8

The sterilization process (that applies γ-rays), the elution test, and the bleed-out phenomenon test were performed in the same manner as in Example 1, except that the vials produced in Example 2 were used, and the exposure was changed to 35 kGy. The results are shown in Table 2.

TABLE 2

| | | Unit | Example 1 | Comparative Example 1 | Comparative Example 2 | Example 2 | Comparative Example 3 |
|---|---|---|---|---|---|---|---|
| Resin composition | [2]-1 | parts by weight | 95 | 100 | 50 | | |
| | [2]-2 | parts by weight | | | | 77 | 90 |
| | [2]-3 | parts by weight | | | | | |
| | [2]-4 | parts by weight | | | | | |
| | [2]-1MP | parts by weight | 5 | | 50 | | |
| | [2]-2MP | parts by weight | | | | 23 | 10 |
| | [2]-3MP | parts by weight | | | | | |
| | [2]-4MP | parts by weight | | | | | |
| Hydrogenation rate | | % | 99.9 | 99.9 | 99.9 | 99.6 | 99.6 |
| Antioxidant (parts by weight)/hydrogenated block copolymer (100 parts by weight) | | parts by weight | 0.098 | 0.050 | 0.525 | 0.269 | 0.145 |
| Value W calculated by expression (1) | E = 25 | — | 0.086 | 0.086 | 0.086 | 0.224 | 0.224 |
| | E = 35 | — | | | | | |
| Before sterilization | | | | | | | |
| Elution test | Difference in pH | — | Good | Good | Good | Good | Good |
| | Foaming | — | Good | Good | Good | Good | Good |
| | UV absorption 220 to 241 nm | — | Good | Good | Good | Good | Good |
| | 241 to 350 nm | — | Good | Good | Good | Good | Good |
| | $KMnO_4$-reducing substance | mL | Good | Good | Good | Good | Good |
| Bleed-out phenomenon | | | Good | Good | Good | Good | Good |
| After sterilization using γ-rays | | | | | | | |
| Exposure of γ-rays | | kGy | 25 | 25 | 25 | 25 | 25 |
| Elution test | Difference in pH | — | Good | Bad | Good | Good | Bad |
| | Foaming | — | Good | Good | Good | Good | Good |
| | UV absorption 220 to 241 nm | — | Good | Good | Good | Good | Good |
| | 241 to 350 nm | — | Good | Good | Good | Good | Good |
| | $KMnO_4$-reducing substance | mL | Good | Good | Good | Good | Good |
| Bleed-out phenomenon | After 30 days | — | Good | Good | Bad | Good | Good |

| | | Unit | Example 3 | Comparative Example 4 | Comparative Example 5 | Comparative Example 6 |
|---|---|---|---|---|---|---|
| Resin composition | [2]-1 | parts by weight | | | | |
| | [2]-2 | parts by weight | | | | |
| | [2]-3 | parts by weight | 58 | 73 | 50 | |
| | [2]-4 | parts by weight | | | | 47 |
| | [2]-1MP | parts by weight | | | | |
| | [2]-2MP | parts by weight | | | | |
| | [2]-3MP | parts by weight | 42 | 27 | 50 | |
| | [2]-4MP | parts by weight | | | | 53 |
| Hydrogenation rate | | % | 99.2 | 99.2 | 99.2 | 98.1 |
| Antioxidant (parts by weight)/hydrogenated block copolymer (100 parts by weight) | | parts by weight | 0.449 | 0.307 | 0.525 | 0.554 |
| Value W calculated by expression (1) | E = 25 | — | 0.408 | 0.408 | 0.408 | 0.914 |
| | E = 35 | — | | | | |
| Before sterilization | | | | | | |
| Elution test | Difference in pH | — | Good | Good | Good | Good |
| | Foaming | — | Good | Good | Good | Good |
| | UV absorption 220 to 241 nm | — | Good | Good | Good | Good |
| | 241 to 350 nm | — | Good | Good | Good | Good |
| | $KMnO_4$-reducing substance | mL | Good | Good | Good | Good |
| Bleed-out phenomenon | | | Good | Good | Good | Good |
| After sterilization using γ-rays | | | | | | |
| Exposure of γ-rays | | kGy | 25 | 25 | 25 | 25 |
| Elution test | Difference in pH | — | Good | Bad | Good | Bad |
| | Foaming | — | Good | Good | Good | Good |
| | UV absorption 220 to 241 nm | — | Good | Good | Good | Good |
| | 241 to 350 nm | — | Good | Good | Good | Good |
| | $KMnO_4$-reducing substance | mL | Good | Good | Good | Good |
| Bleed-out phenomenon | After 30 days | — | Good | Good | Bad | Bad |

| | | Unit | Example 4 | Comparative Example 7 | Example 5 | Comparative Example 8 |
|---|---|---|---|---|---|---|
| Resin composition | [2]-1 | parts by weight | 85 | 95 | | |
| | [2]-2 | parts by weight | | | 65 | 77 |
| | [2]-3 | parts by weight | | | | |
| | [2]-4 | parts by weight | | | | |
| | [2]-1MP | parts by weight | 15 | 5 | | |
| | [2]-2MP | parts by weight | | | 35 | 23 |
| | [2]-3MP | parts by weight | | | | |
| | [2]-4MP | parts by weight | | | | |

TABLE 2-continued

| | | | | | | |
|---|---|---|---|---|---|---|
| Hydrogenation rate | | % | 99.9 | 99.9 | 99.6 | 99.6 |
| Antioxidant (parts by weight)/hydrogenated block copolymer (100 parts by weight) | | parts by weight | 0.193 | 0.098 | 0.383 | 0.269 |
| Value W calculated by expression (1) | E = 25 | — | — | 0.120 | 0.314 | 0.314 |
| | E = 35 | | | | | |
| | | Before sterilization | | | | |
| Elution test | Difference in pH | — | Good | Good | Good | Good |
| | Foaming | — | Good | Good | Good | Good |
| | UV absorption 220 to 241 nm | — | Good | Good | Good | Good |
| | 241 to 350 nm | — | Good | Good | Good | Good |
| | KMnO$_4$-reducing substance | mL | Good | Good | Good | Good |
| Bleed-out phenomenon | | — | Good | Good | Good | Good |
| | | After sterilization using γ-rays | | | | |
| | Exposure of γ-rays | kGy | 35 | 35 | 35 | 35 |
| Elution test | Difference in pH | — | Good | Bad | Good | Bad |
| | Foaming | — | Good | Good | Good | Good |
| | UV absorption 220 to 241 nm | — | Good | Good | Good | Good |
| | 241 to 350 nm | — | Good | Good | Good | Good |
| | KMnO$_4$-reducing substance | mL | Good | Good | Good | Good |
| Bleed-out phenomenon | After 30 days | — | Good | Good | Good | Good |

Reference Example 9

Preparation of Resin Composition [2]-11 Including Hydrogenated Block Copolymer and Antioxidant 0.14 parts by weight of 3,9-bis(2,6-di-t-butyl-4-methylphenoxy)-2,4,8,10-tetraoxa-3,9-diphosphaspiro[5.5]undecane ("ADK STAB (registered trademark) PEP-36" manufactured by Adeka Corporation) (phosphorus-based antioxidant) was added to 100 parts by weight of the pellets of the resin composition [2]-1 including the hydrogenated block copolymer [1]-1 and the antioxidant (prepared in Reference Example 1), and the mixture was processed (kneaded using a twin-screw kneader, extruded in the shape of a strand, and cut using a pelletizer) in the same manner as in Reference Example 5 to obtain 95 parts of pellets of a resin composition [2]-11 including the hydrogenated block copolymer [1]-1 and the antioxidant.

The resin composition [2]-11 included the antioxidant in a ratio of 0.190 parts by weight (in total) based on 100 parts by weight of the hydrogenated block copolymer [1]-1.

The ratio "wA:wB" was 50:50, the weight average molecular weight (Mw) was 65,600, and the hydrogenation rate was 99.9%.

The value W calculated by the expression (1) (when the exposure E is 25 kGy) was 0.086 parts by weight (i.e., the resin composition [2]-11 included the antioxidant in a ratio of more than W parts by weight (in total)).

Comparative Example 9

A vial was produced, and the sterilization process (that applies γ-rays) and the elution test were performed in the same manner as in Example 1, except that the pellets of the resin composition [2]-11 prepared in Reference Example 9 were used.

As a result, the difference in pH with respect to the blank sample was −1.0 or more (i.e., a decrease in pH was not sufficiently suppressed). On the other hand, defoaming occurred within 3 minutes. The difference in absorbance at 220 to 241 nm with respect to the blank sample was 0.08 or less, and the difference in absorbance at 241 to 350 nm with respect to the blank sample was 0.05 or less. The difference in consumption of the potassium permanganate solution was 1.0 mL or less.

Reference Example 10

Preparation of Resin Composition [2]-12 Including Hydrogenated Block Copolymer and Antioxidant 0.14 parts by weight of 1,3,5-tris(3,5-di-t-butyl-4-hydroxyphenylmethyl)-2,4,6-trimethylbenzene ("ADK STAB (registered trademark) AO-330" manufactured by Adeka Corporation) (phenol-based antioxidant) was added to 100 parts by weight of the pellets of the resin composition [2]-1 including the hydrogenated block copolymer [1]-1 and the antioxidant (prepared in Reference Example 1), and the mixture was processed (kneaded using a twin-screw kneader, extruded in the shape of a strand, and cut using a pelletizer) in the same manner as in Reference Example 5 to obtain 96 parts of pellets of a resin composition [2]-12 including the hydrogenated block copolymer [1]-1 and the antioxidant.

The resin composition [2]-12 included the antioxidant in a ratio of 0.190 parts by weight (in total) based on 100 parts by weight of the hydrogenated block copolymer [1]-1.

The ratio "wA:wB" was 50:50, the weight average molecular weight (Mw) was 65,600, and the hydrogenation rate was 99.9%.

The value W calculated by the expression (1) (when the exposure E is 25 kGy) was 0.086 parts by weight (i.e., the resin composition [2]-12 included the antioxidant in a ratio of more than W parts by weight (in total)).

Example 6

A vial was produced, and the sterilization process (that applies γ-rays) and the elution test were performed in the same manner as in Example 1, except that the pellets of the resin composition [2]-12 prepared in Reference Example 10 were used.

As a result, the difference in pH with respect to the blank sample was 1.0 or less (i.e., a significant decrease in pH was not observed) (i.e., a decrease in pH was suppressed). Defoaming occurred within 3 minutes. The difference in absorbance at 220 to 241 nm with respect to the blank sample was 0.08 or less, and the difference in absorbance at 241 to 350 nm with respect to the blank sample was 0.05 or less. The difference in consumption of the potassium permanganate solution was 1.0 mL or less.

The following were confirmed from the results obtained in the examples and the comparative examples.

The medical container according to the invention was obtained using the resin composition including the hydrogenated block copolymer having a hydrogenation rate of 99% or more, and the phenol-based antioxidant in a ratio of W parts by weight or more (the value W corresponds to the exposure of high-energy rays used for the sterilization process and is calculated by the expression (1)), and did not show a significant change in pH due to elution in water as a result of the sterilization process that applies high-energy rays (Examples 1 to 6).

When the ratio (amount) of the phenol-based antioxidant was less than W parts by weight (calculated by the expression (1)), a significant change in pH due to elution in water occurred as a result of the sterilization process that applies high-energy rays (Comparative Examples 1, 3, 4, and 6 to 8).

When the ratio (amount) of the phenol-based antioxidant was less than W parts by weight (calculated by the expression (1)), and the total ratio (amount) of the antioxidant was adjusted to be equal to or more than W parts by weight by adding the phosphorus-based antioxidant, a significant change in pH due to elution in water occurred as a result of the sterilization process that applies high-energy rays Comparative Example 9

When the ratio (amount) of the phenol-based antioxidant exceeded 0.5 parts by weight based on 100 parts by weight of the hydrogenated block copolymer, a significant change in pH due to elution in water as a result of the sterilization process that applies high-energy rays did not occur, but a bleed-out phenomenon of the antioxidant on the surface of the formed article occurred with the passage of time (Comparative Examples 2, 5, and 6).

INDUSTRIAL APPLICABILITY

The method according to the invention that sterilizes a medical formed article formed of a resin composition that includes a specific hydrogenated block copolymer and a specific amount of a phenol-based antioxidant by applying high-energy rays, can suppress a situation in which a significant change in pH due to elution in water occurs, and the medical formed article used in connection with the invention exhibits excellent heat resistance, low elution properties, excellent content visibility, and the like, and is useful as a medical formed article.

The invention claimed is:

1. A method for producing a sterilized medical formed article comprising applying high-energy rays to a medical formed article at an exposure E, the medical formed article being formed of a resin composition that comprises a hydrogenated block copolymer and a phenol-based antioxidant, the hydrogenated block copolymer being obtained by hydrogenating 99% or more of unsaturated bonds of a block copolymer that comprises at least two polymer blocks [A] and at least one polymer block [B], the polymer block [A] comprising a repeating unit derived from an aromatic vinyl compound as a main component, the polymer block [B] comprising a repeating unit derived from a linear conjugated diene compound as a main component, and a ratio (wA:wB) of a weight fraction wA of the polymer block [A] in the block copolymer to a weight fraction wB of the polymer block [B] in the block copolymer being 30:70 to 70:30, and the resin composition comprising the phenol-based antioxidant in a ratio of W to 0.50 parts by weight based on 100 parts by weight of the hydrogenated block copolymer, W being calculated by an expression (1), $$W=[0.46\times(100-H)+0.04]\times(E/25) \qquad (1)$$

where, W is the ratio (parts by weight) of the phenol-based antioxidant based on 100 parts by weight of the hydrogenated block copolymer, H is the hydrogenation rate (%) of the hydrogenated block copolymer, H is a numerical value from 99 to 100, and E is the exposure (kGy) of the high-energy rays.

2. The method for producing a sterilized medical formed article according to claim 1, wherein the high-energy rays are γ-rays or electron beams.

3. The method for producing a sterilized medical formed article according to claim 1, wherein the high-energy rays are applied in a state in which the medical formed article is contained in an airtight container that is formed of a resin film.

* * * * *